Figure 1:
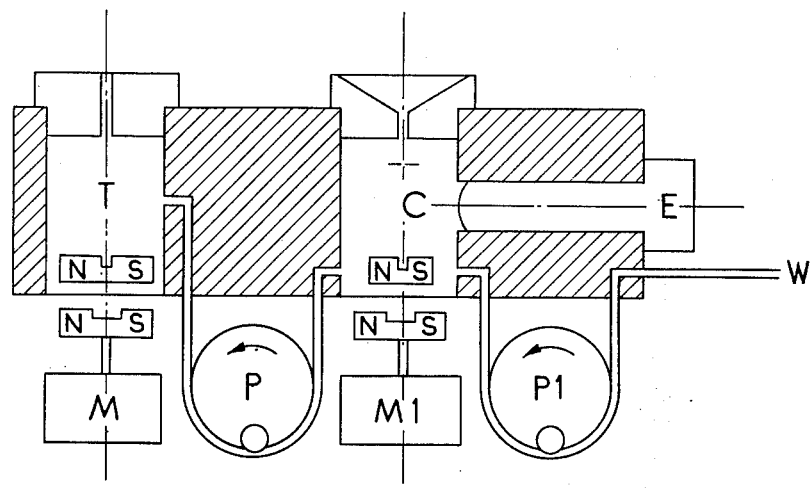

United States Patent [19]

Raffaele

[11] 4,013,417
[45] Mar. 22, 1977

[54] ANALYZER FOR THE DETERMINATION OF HEMOGLOBIN AND OTHER RELATED COMPOUNDS IN WHOLE BLOOD AND HEMOGLOBIN SOLUTIONS

[75] Inventor: Italo Raffaele, Milan, Italy

[73] Assignee: Biomedix A.G., Vaduz, Liechtenstein

[22] Filed: July 31, 1975

[21] Appl. No.: 600,802

[30] Foreign Application Priority Data

Aug. 9, 1974 Italy .................................. 26213/74

[52] U.S. Cl. ........................... 23/253 R; 23/230 B; 235/151.35; 356/40; 356/41
[51] Int. Cl.² .................. G01N 33/16; G01N 21/26
[58] Field of Search ............. 23/230 B, 253 R, 259; 356/40, 41, 72, 184; 235/151.13, 151.35

[56] References Cited

UNITED STATES PATENTS

| | | | |
|---|---|---|---|
| 3,622,795 | 11/1971 | Dorman, Jr. et al. | 356/40 X |
| 3,764,267 | 10/1973 | Farr | 356/40 X |
| 3,804,535 | 4/1974 | Rodriguez | 356/41 X |
| 3,825,342 | 7/1974 | Lubbers et al. | 356/41 |
| 3,854,878 | 12/1974 | Kiesow | 356/41 X |
| 3,874,850 | 4/1975 | Sorenson et al. | 23/230 B |

FOREIGN PATENTS OR APPLICATIONS 990,540   4/1965   United Kingdom ................ 356/41

*Primary Examiner*—R.E. Serwin
*Attorney, Agent, or Firm*—Cushman, Darby & Cushman

[57] ABSTRACT

This specification describes a new analyzer for the determination of total hemoglobin; percent oxyhemoglobin, deoxyhemoglobin, methmoglobin, sulfhemoglobin; and oxygen capacity in a micro sample (5 to 10 $\mu$l) of hole human blood. The essential components of the analyzer are (1) a cuvette in which simultaneous measurements of $PO_2$ (by an oxygen electrode) and absorbance (by a dual wavelength optical system) are made, (2) an automatic pump system for filling and emptying the cuvette, (3) an equilibrating tonometer to equilibrate the reagent with air or another gas phase, (4) electronic circuits for the measurement of light intensity and oxygen pressure, (5) an analogue computer, and (6) a printer. Other essential parts of the invention are (a) original procedures and (b) ad hoc developed physico-chemical equations.

10 Claims, 4 Drawing Figures

Hydraulic scheme

Hydraulic scheme

Optical scheme

ANALYZER FOR THE DETERMINATION OF HEMOGLOBIN AND OTHER RELATED COMPOUNDS IN WHOLE BLOOD AND HEMOGLOBIN SOLUTIONS

SUMMARY OF THE INVENTION

This invention is concerned with an analyzer for determining the concentration of total hemoglobin and its derivatives of clinical and physiological interest. The art of determining such substances is well known in the clinico-chemistry practice. This art pertains to the clinico-chemical, physiological, biochemical, and clinical fields, and further comments there about are unnecessary for further understanding of the invention. It will be of interest to recall that no instrument has yet been either produced commercially or described in the literature to carry out the simultaneous determination of the following parameters: total hemoglobin, percent oxyhemoglobin, deoxyhemoglobin, methemoglobin, sulfhemoglobin, and oxygen capacity. General information concerning this matter can be found in the article "Determination of hemoglobin and its derivatives" (E. J. Van Kampen and W. G. Zijlstra, Adv. Clin. Chem., 8: 141, 1965) and in chapter 23 "Hemoglobins, myoglobins, and haptoglobins" of the reference textbook Clinical Chemistry — Principles and Techniques (R. J. Henry, D. C. Cannon, and J. W. Winkelman, eds., Harper and Row Publishers, New York, 1974).

The instrument object of this invention features unprecedented speed and ease of operation and, for the first time, allows the simultaneous determination of hemoglobin and all its derivatives of clinical interest in micro samples (5 to 10 $\mu$l) of whole blood. The instrument described in this application greatly improves the art and technology of previously described methods and instrumentation with regard to both the time and sample volume required to attain the desired measurements and the manner by which measurements of the desired type and precision can be attained.

In its broadest aspect the analyzer comprises (1) a tonometer, where a buffer of a given composition is kept in equilibrium with air, a pump for the transfer of liquid from the tonometer into a cuvette which contains the sensitive part of a $PO_2$ electrode, and another pump for the automatic emptying of the cuvette; (2) a dual wavelength system and associated light intensity sensors and amplifiers; (3) an analogue computer for the programming of the automatic cycle of measurements and calculations of final concentrations, (4) three digital displays for visualising certain required parameters, and (5) a printer to print the results according to an automatic cycle under computer control. System (1) and (2) are thermostated by a separate sensor and heater arrangement. These and other important objects, features, and advantages of the invention will be further apparent from the following detailed description of the same invention, taken together with accompanying drawings, (photographs), and details of new and original chemical procedures and equations for calculation of relevant parameters to form the essential components of this disclosure.

DESCRIPTION OF PARTICULAR EMBODIMENTS

The general line of thought yielding the advantage of the invention around which components (1) to (5) described in the previous section have been designed, constructed, and assembled so to give the unique functions of the instrument subject of this invention, can be understood from the following considerations.

Only one instrument has been designed and marketed for the simultaneous determination of hemoglobin and certain of its derivatives in an automatic way. The measurements are limited to the macro (0.5 to 1.0 ml) estimation of total hemoglobin, and percent oxyhemoglobin and carboxyhemoglobin ("Spectrophotometric determination of hemoglobin concentration and percent oxyhemoglobin and carboxyhemoglobin saturation", by Malenfant et al. presented at the 20th National Meeting of the American Association of Clinical Chemists, Aug. 19, 1968). This instrument assumes that the concentration of methemoglobin and sulfhemoglobin are both equal to zero. The presence of clinically significant values of such derivatives produces, however, an erroneous and unpredictable reading of the other measured parameters. The only other way (besides that possible by the afore mentioned commercial instrument) of measuring hemoglobin and its derivatives is, at the present time, represented by a combination of manual procedures which require much time, sample volume, and skill (Henry et al., ibidem). In addition, traditional techniques pose certain drastic limitations to instrument design, accuracy, and reproducibility of results.

The most critical question that is common to all methods so far proposed, manual or automatic, is the measurement of the proportion of deoxy- and oxyhemoglobin present in any given blood sample. In order not to change this proportion it is necessary that the whole blood sample be hemolysed and also handled anaerobically, if measurements of the actual saturation in the original sample are to be made. Thus dilution of the blood sample with hemolysing agents should be kept to a minimum. If, on the other hand, the freeze-and-thaw method of hemolysis is used (no dilution), significant turbidity develops preventing accurate (i.e., on the absolute basis) absorbance readings.

In both cases, due to the high absorbance of whole blood, it is necessary to use for spectrophotometric measurements a very short path length absorption cell (0.1 mm or less). Users of available instrumentation are well aware of the many practical difficulties encountered in the measurement of absorbances in such cells (i.e., frequent clogging of the thin cuvettes, inaccurate readings due to the presence of difficult to dislodge air bubbles or fibrin clots, and incomplete hemolysis of blood with associated unpredictable turbidity). Calculation of concentrations of hemoglobin, percent oxy- and carboxyhemoglobin as actually done in existing instrumentation assume constancy and reproducibility of optical paths. Dismounting and cleaning the thin optical cells (0.1 mm or less) often requires complete recalibration of the instrument. In addition the simultaneous measurement at three wavelengths of deoxy-, oxy-, and carboxyhemoglobin does not allow slight variation in filter characteristics such as in peak wavelengths and wavelength band pass shape to occur. All the afore mentioned difficulties are now obviated by the innovating principles of this invention.

In order to obtain a reasonable value of absorbance in an ordinary 1.0 cm light path cuvette, normal blood must be diluted ca 100 times. As the normal oxygen content (combined plus dissolved) of human blood is close to 10 millimoles of oxygen per liter, a 100-fold dilution will change this concentration to 0.1 mM. Water or buffers used for dilution, when in equilibrium with air, contain (at 30°) ca 0.235 mM dissolved oxygen. The above figures make it clear that the dilution of blood in buffers in equilibrium with air will change the total oxygen content and considerably affect the proportion of oxy- and deoxyhemoglobin. The problem of diluting the blood to give a reasonable optical absorbance without altering the proportion of deoxy- to oxyhemoglobin in an unpredictable way can be solved if the dilution is made to occur in a cuvette (under practically anaerobic conditions) where the oxygen pressure is continuously monitored. The experimental system adopted in the instrument described in this patent application is schematically shown in FIGS. 1 and 2.

Figure 2:
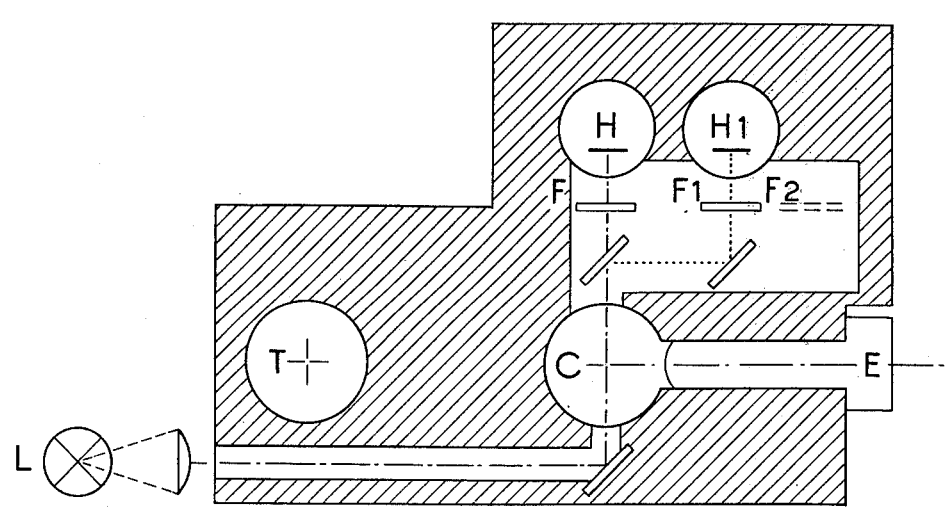
Figure 3:
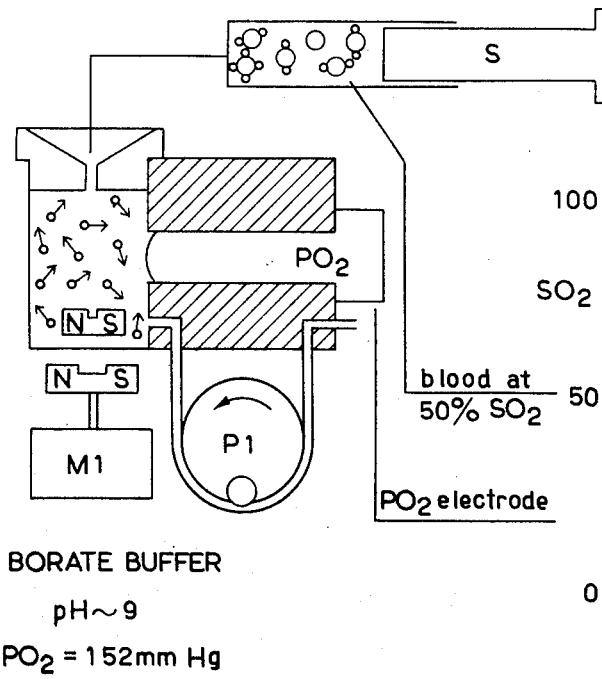
Figure 3:
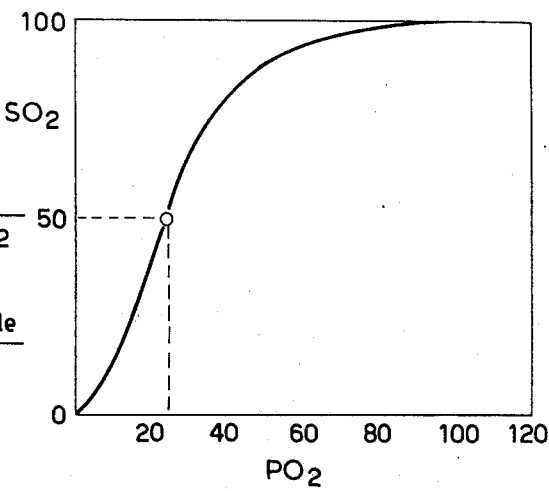
Figure 4:
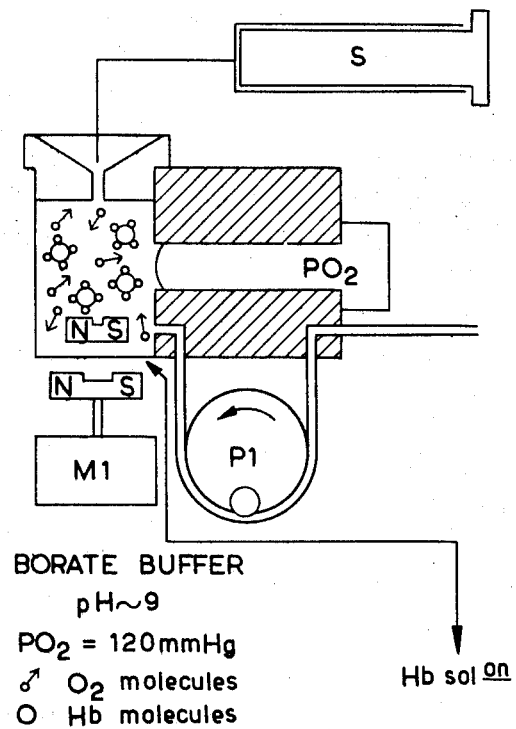
Figure 4:
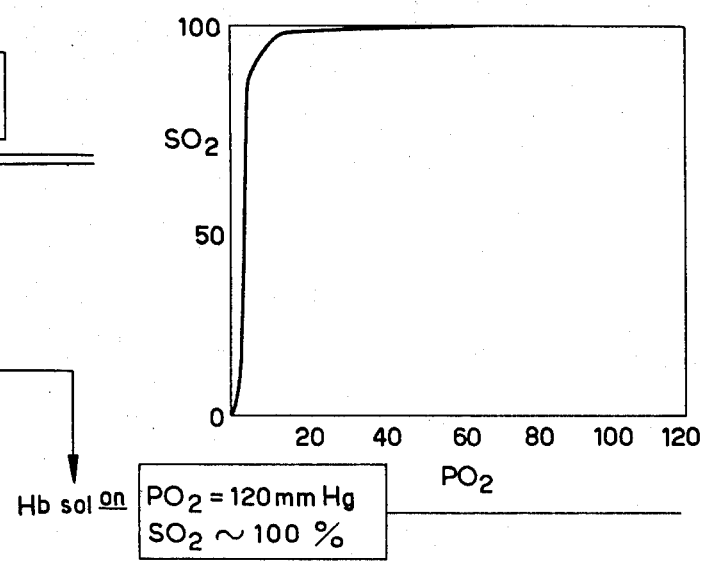

FIG. 1 shows the hydraulic scheme of the apparatus.
FIG. 2 shows the optical scheme.
FIGS. 3 and 4 illustrate examples of the system in use.

T is a tonometer containing a borate buffer at pH 9.2 plus an appropriate amount of Sterox SE (a hemolysing agent). The buffer is kept in equilibrium with air by magnetic stirring. At the start of the analysis pump P, under automatic control, fills cuvette C. The content of this cuvette is also stirred by the separate motor M1. C is an optical curvette containing the sensitive part of an oxygen electrode (E). A tungsten lamp L and a lens provide a light beam which is passed through cuvette C and then analysed at selected wavelengths by photo multipliers H and H1 and associated electronic circuit (not shown in the figure). F and F1 are two precision interference filters centered at 497 and 565 nm wavelength. F1 can be automatically interchanged with F2, another interference filter centered at 620 nm. An understanding of the functioning of the analyzer can be obtained from the following example (see FIGS. 3 and 4).

Before whole blood is introduced in cuvette C, electrode E will record the $PO_2$ of the buffer previously equilibrated with air in tonometer T. If, for instance, the barometric pressure is 760 mm and the temperature 30°, the buffer will have a $PO_2$ of $0.2093 \cdot (760 - 32) \cong 152.4$ mm Hg. Suppose now that 10 μl of a blood sample containing hemoglobin at a concentration of 10 mEq/heme per liter (16 g%), 50% saturated with oxygen, be introduced into the cuvette from syringe S. Assuming a 100-fold dilution, the final hemoglobin concentration in C will be 0.1 mEq/heme per liter and the total oxygen content contributed by the hemoglobin 0.05 mM oxygen. In the borate buffer, at pH 9.2, 30°, hemoglobin can be considered completely saturated with oxygen at an oxygen pressure of 20 to 25 mm. Thus as the hemoglobin was initially 50% saturated, 0.05 mM of oxygen must be taken up by the deoxyhemoglobin to reach 100% oxygenation. The oxygen electrode will thus record a decrease in $PO_2$ which will be proportional to the initial sample oxygen saturation. (For the example just given, as the oxygen initially present in the borate buffer was 0.235 mM [this is the dissolved oxygen in the borate buffer in equilibrium with a $PO_2$ of 152 mm Hg], the total oxygen left in solution after hemoglobin has become completely oxygenated will be $0.235 - 0.05 = 0.185$ mM corresponding to a $PO_2$ of $[0.185/0.235] \times 152 \cong 120$ mm Hg.)

Thus the critical point of measuring the oxygen saturation of a blood sample while diluting it has been solved by the apparatus and the procedures adopted in this invention by allowing the dilution to proceed in a solution whose $PO_2$ is constantly monitored. At the end of the dilution and $\Delta PO_2$ measurement the clear oxyhemoglobin solution can be analysed by the three wavelength system shown in FIG. 2 at 565, 497, and 620 for carboxyhemoglobin, methemoglobin, and sulfhemoglobin, respectively, allowing the complete qualitative determination of hemoglobin and its derivatives to be made in an approximate time of 1 minute.

It should be made clear that the oxygen electrode has already been used in the past to measure the oxygen content of a blood sample, i.e., by mixing the blood with ferricyanide ("Blood oxygen content measurements using the oxygen electrode", M. B. Laver, A. J. Murphy, A. Serfen, and E. P. Redford, J. Appl. physiol., 20: 1063, 1965) or with carbon monoxide ("Blood oxygen content measured by oxygen tension after release by carbon monoxide", C. H. Klingenmaier, M. G. Behar, and T. C. Smith, J. Appl. Physiol., 26: 653, 1965). However, this or similar methods have the disadvantage that some of the derivatives of hemoglobin are transformed in an irreversible, unaccountable way which prevents their further determination. The specific transformation of deoxyhemoglobin, coupled with its simultaneous determination by the oxygen electrode by dilution in the alkaline buffer, does not alter the concentration of other forms of hemoglobin such as methemoglobin, carboxyhemoglobin, and sulfhemoglobin.

Specific transformation and disappearance of deoxyhemoglobin allows the adoption in the instrument design of certain points on the absorption curve of methemoglobin, sulfhemoglobin, carboxyhemoglobin, and total hemoglobin which have inherent advantages (broader parts of the spectrum) over the very narrow band width light beams which have to be used if deoxyhemoglobin is still present in solution. In addition, dilution of blood with a 100-fold excess of hemolysing diluent does effectively eliminate turbidity in the solution. The rather alkaline pH of the buffer used also prevents precipitation of plasma protein, a phenomena well known to clinico-chemists and hematologists.

The application of these new ideas and the instrument design originating therefrom allows the formulation of some original chemical procedures and ways of calculation of all other hemoglobin derivatives.

1. Calculation of deoxyhemoglobin

The total oxygen present in the borate buffer before mixing blood at unknown oxygen saturation S will be given by $$QO_2{}^B = [O_2 \text{ dissolved}] \times V_o$$

where $V_o$ is the volume of the borate buffer in cuvette C. After adding to the buffer (but before mixing) a volume $V_B$ of blood into cuvette C, the total oxygen present in the volume $V_o$ of cuvette C will be, since $V_o$ is constant and $V_B$ displaces an equal amount of buffer, $$TO_2 = [O_2 \text{ combined in blood}] \times V_B + [O_2 \text{ dissolved in blood}] \times V_B + [O_2 \text{ dissolved in buffer}] (V_o - V_B) \quad [1]$$

Immediately after the fisical mixing of buffer with blood, any chemical reaction in the system will reach equilibrium in a very short time. The total oxygen in the mixture after this step will then be $$TO_2 = [O_2 \text{ combined}']V_o + [O_2 \text{ dissolved}']V_o \quad [2]$$

where [$O_2$ combined'] is the concentration of oxygen combined in the diluted blood-buffer solution. If S is the initial and S' the final oxygen saturation of hemoglobin, combining eqs. [1] and [2], since [Cap'] = [Cap]$V_B/V_o$ and S[Cap] = $O_2$ combined, then $$\frac{V_B S[Cap] + \alpha V_B PO_2 + \alpha'(V_o - V_B)PO_2' = SV_o'}{[Cap'] + \alpha' V_o PO_2''} \quad [3]$$

where [Cap] is the concentration of hemoglobin able to combine with oxygen (= deoxyhemoglobin plus oxyhemoglobin), $\alpha$ is the coefficient of oxygen solubility in blood, $\alpha'$ is the coefficient of oxygen solubility in the borate buffer, $PO_2$ is the oxygen pressure of the blood sample, $PO_2'$ the initial oxygen pressure of borate buffer, and $PO_2''$ that of the blood-borate mixture. If $PO_2''$ is high enough (i.e., > 20 mm Hg) to completely saturate the hemoglobin present, then S' = 1 and eq. [3] will transform into

[Cap] (1 − S) = deoxyhemoglobin in the original sample $$= \frac{\alpha' V_0(PO_2' - P''O_2'') + V_B(PO_2 \alpha - P'O_2' \alpha')}{V_B} \quad [4]$$

In this equation the experimentally available parameters are $PO_2'$ and $PO_2$, i.e., the oxygen pressure in equilibrium with the borate buffer before and after mixing. $PO_2$, the oxygen pressure in equilibrium with the original blood sample, can also be measured separately if a more exacting value of deoxyhemoglobin is required. For normal clinical use, where an error in the deoxyhemoglobin concentration equal to ±1% of the total hemoglobin is not significant, eq. [4] can be approximated by $$[\text{deoxyhemoglobin}] = \frac{\alpha' V_0(PO_2' - P''O_2'') + (100\alpha - P'O_2'\alpha')}{V_B} \quad [5]$$

2. Determination of total hemoglobin

After the blood sample has been diluted with the alkaline borate buffer and deoxyhemoglobin completely and specifically transformed into oxyhemoglobin, the hemoglobin derivatives present in solution will be oxyhemoglobin, carboxyhemoglobin, methemoglobin, and sulfhemoglobin. Analysis of the absorption spectrum of oxy- and carboxyhemoglobin (Van Kampen and Zijlstra, ibidem) shows that their absorption curves are isosbestic (and also have a rather low absorbance value) at 497 nm. In addition, at this wavelength the value of the derivative $dA/d\lambda$ is close to zero (broad part of the spectrum), a fact which thus allows the use of interference filters with broader band width and not so stringent requirements of stability. In the analyzer it is possible, by means of two digital switches positioned in the front panel, to subtract from the total absorbance of the solution ($A_{497}$) the sum of the absorbances due to the presence of sulfhemoglobin plus methemoglobin. If $\epsilon_{497}^4$ and $\epsilon_{497}^5$ are the absorption coefficients of methemoglobin and sulfhemoglobin at 497 nm in mEq/heme per liter, and [metHb] and [sulfHb] their concentration in mEq/-heme per liter (to be later determined) the absorbance contributed at 497 nm by the sum of these derivatives will be $$A_{497}^{met + sulf} = \epsilon_{497}^4 [\text{metHb}] + \epsilon_{497}^5 [\text{sulfHb}] \quad (6)$$

Since [metHb] = K [Hb tot], [SulfHb] = K'[Hb tot], and [Hb tot] = [$HbO_2'$] + [HbCO] + [metHb] + [suldHb], then $$A_{497} = \epsilon_1 ( [HbO_2] + [HbCO] ) + \epsilon_{497}^4 [\text{metHb}] + \epsilon_{497}^5 [\text{sulfHb}] \quad (7)$$

and $$[\text{Hb tot}] = \frac{A_{497}}{(1 - K - K') + \epsilon_{497}^4 K + \epsilon_{497}^5 K'} \quad (8)$$

3. Determination of carboxy- and oxyhemoglobin

The electronic circuits of the analyzer, after determining the values of deoxyhemoglobin and total hemoglobin concentration, reads the absorbance of the solution at 565 and 497 nm. The absorption due to the presence of [$HbO_2$]' and [HbCO] in solution is obtained from the following equations.

$$A'_{497} = A_{497} - \epsilon_{497}^4 [\text{metHb}] - \epsilon_{497}^5 [\text{sulfHb}]$$

$$= \epsilon_{497}^1 ( [HbO_2] + [HbCO] ) \quad (9)$$

$$A'_{565} = A_{565} - \epsilon_{565}^4 [\text{metHb}] - \epsilon_{565}^5 [\text{sulfHb}]$$

$$= \epsilon_{565}^1 [HbO_2] + \epsilon_{565}^2 [HbCO] \quad (10)$$

From $A_{497}'$ and $A_{565}'$ the relative proportion of oxy- and carboxyhemoglobin can be obtained from the formula reported by Van Kampen and Zijlstra (ibidem). This calculation is automatically done by the analogue computer of the analyzer.

4. Determination of metHb at 620 nm

Filter F2, FIG. 2, is an interference filter which is automatically inserted between the light source and the photomultiplier (H2) as soon as deoxyhemoglobin, total hemoglobin, and percent carboxyhemoglobin have been determined. The following equation applies:

$$A_{620} = \epsilon_{620}^1 [HbO_2]' + \epsilon_{620}^2 [HbCO]$$

$$+ \epsilon_{620}^4 [\text{metHb}] + \epsilon_{620}^5 [\text{sulfHb}] \quad (11)$$

If a suitable amount of potassium cyanide or acid buffer is introduced into the cuvette, $A_{620}$ will change because (i) methemoglobin is specifically transformed into cyanomethemoglobin (or, in the case of the acid, the spectrum of methemoglobin is changed by the pH change) and (ii) dilution of solution with either of the two reagents. From the known change of optical density and the knowledge of the absorption coefficients of cyanomethemoglobin (or methemoglobin at the new pH) the concentration of methemoglobin in the original sample is automatically calculated by the analogue computer of the analyzer.

5. Determination of sulfHb at 620 nm

The residual absorption at 620, $A_{620}'$, eq. (11), when corrected for the absorption due to the presence in solution of [HbCO], [HbO$_2$], and [metHb] (each multiplied by a suitable factor), gives the concentration of sulfhemoglobin in solution. The correctly determined values of metHb and sulfHb can now be inserted (when present in significant amounts) by the appropriate digital switches into the computing system, thus allowing the correct determination of all other parameters.

6. Determination of percent carboxyhemoglobin, oxyhemoglobin, methemoglobin, and sulfhemoglobin and oxygen capacity Such parameters are calculated automatically from the known concentrations of the various derivatives, according to the formulas $$\% \text{ oxyhemoglobin} = \frac{[\text{oxyhemoglobin}]}{[\text{Total Hb}] - [\text{metHb}] - [\text{sulfHb}] - [\text{COHb}]} \quad (12)$$

$$\% \text{ carboxyhemoglobin} = \frac{[\text{HbCO}]}{[\text{total Hb}] - [\text{metHb}] - [\text{sulfHb}]} \quad (13)$$

$$\% \text{ methemoglobin} = \frac{[\text{metHb}]}{[\text{total Hb}]} \quad (14)$$

$$\% \text{ sulfhemoglobin} = \frac{[\text{sulfHb}]}{[\text{total Hb}]} \quad (15)$$

$$O_2 \text{ capacity (ml\%)} = ([\text{HbO}_2] + [\text{deoxyhemoglobin}]) \quad (16)$$

The analogue computer of the analyzer automatically sends the instructions (according to eqs. [12] to [16]) to print the relevant data to the printer incorporated in the instrument.

While the details of the new instrument have been described with specific reference to a complete procedure of analysis, it is evident that the invention should not be and is not limited thereto, and that numerous equivalent devices might be devised by those skilled in the art from the teaching of the invention. Furthermore, it is evident that the same device can be combined with and/or complemented by additional devices and means without departing from the spirit and purpose of the invention. For instance, by limiting the system (a) to an oxygen electrode and using a combination of borate buffer and ferricyanide reagent, % saturation and total oxygen content of the blood sample can be obtained; and (b) to an oxygen electrode and observation at one wavelength, deoxyhemoglobin and other parameters can be obtained.

What I claim is:

1. An analyzer for the automatic testing of samples of 5 to 10 μl of hemoglobin solutions, particularly whole blood, and for the automatic determination of the total hemoglobin and of the percentage contents of at least the deoxyhemoglobin, the carboxyhemoglobin and the oxyhemoglobin, and/or the ratio of the third to the first component, comprising a tonometer, in which a buffer is kept in equilibrium with a gas having a predetermined oxygen partial pressure, a first pump for the transfer of the liquid to be tested to a cuvette, an oxygen electrode, the sensitive part of which is contained within said cuvette in contact with the said liquid, a second pump for emptying the cuvette, a dual wavelength optical system for measuring the absorbances of the liquid present in the cuvette at the wavelengths of 497 and 565 nm, light sensors adapted to sense the light passing through said optical system, computer means adapted to be fed with electrical signals, respectively corresponding to the values sensed by the oxygen electrode and by the said light intensity sensors, and to process said signals according to the equations:

$$[\text{Hb tot}] = \frac{A_{497}}{(1 - K - K') + \epsilon_{497}^4 K + \epsilon_{497}^5 K'},$$

$$\% \text{ oxyhemoglobin} = \frac{[\text{oxyhemoglobin}]}{[\text{total Hb}] - [\text{metHb}] - [\text{sulfHb}] - [\text{COHb}]},$$

and $$\% \text{ carboxyhemoglobin} = \frac{[\text{HbCO}]}{[\text{total Hb}] - [\text{metHb}] - [\text{sulfHb}]},$$

and display means adapted to display the results of the calculations carried out by said computer means.

2. An analyzer according to claim 1, wherein said optical system consists of a light source and at least two interference filters, centered at 497 and 565 nm wavelength, and adapted to intercept the light beam emitted from said source and passing through the cuvette containing both the sample to be tested and the buffer.

3. An analyzer according to claim 1, wherein the said light intensity sensors consists of photomultipliers, whose output, in form of an electric signal is fed to the said computer means.

4. An analyzer according to claim 1, wherein said computer means are an analogue computer.

5. An analyzer according to claim 1, including said buffer and wherein said buffer is adapted to adjust the pH of the sample being tested to an alkaline value, higher than 8.5.

6. An analyzer according to claim 5, wherein said buffer is a borate buffer and the pH is adjusted at 9.2.

7. An analyzer according to claim 1 further including means for measuring the percentage contents of the methemoglobin and of the sulfhemoglobin, means for measuring the absorbance of the sample being tested at 620 nm wavelength, sensor means adapted to sense the resulting light intensity and to feed the said computer means with an electric signal, said computer means being adapted to calculate the desired contents according to the equations:

$$\% \text{ methemoglobin} = \frac{[\text{metHb}]}{[\text{total Hb}]},$$

and $$\% \text{ sulfhemoglobin} = \frac{[\text{sulfHb}]}{[\text{total Hb}]}.$$

8. An analyzer according to claim 7, wherein said means adapted to measure the absorbance of the sample at 620 nm wavelength consist of a third filter centered at the said wavelength, the sample being added with an agent capable of specifically changing the absorbance of methemoglobin, said agent being selected from the group consisting of potassium cyanide and acid buffers.

9. An analyzer according to claim 1, wherein printing means are connected to the said display means in order to print the results of the computer calculations.

10. An analyzer according to claim 1, wherein the said computer means includes means for calculating the $O_2$ capacity of the sample according to the equation:

$$O_2 \text{ capacity (ml\%)} = f ([HbO_2] + [\text{deoxyhemoglobin}]).$$

* * * * *